United States Patent [19]
Teoule et al.

[11] Patent Number: 5,837,859
[45] Date of Patent: Nov. 17, 1998

[54] PREPARATION OF A ELECTRONICALLY CONDUCTIVE POLYMER/NUCLEOTIDE COPOLYMER

[75] Inventors: Robert Teoule, Grenoble; André Roget, Saint Egreve; Thierry Livache, Grenoble; Christelle Barthet, Grenoble; Gérard Bidan, Grenoble, all of France

[73] Assignee: Cis Bio International, Saclay, France

[21] Appl. No.: 525,506

[22] PCT Filed: Mar. 30, 1994

[86] PCT No.: PCT/FR94/00354

§ 371 Date: Sep. 22, 1995

§ 102(e) Date: Sep. 22, 1995

[87] PCT Pub. No.: WO94/22889

PCT Pub. Date: Oct. 13, 1994

[30] Foreign Application Priority Data

Mar. 31, 1993 [FR] France ................... 93 03732

[51] Int. Cl.⁶ ................. C07H 1/02; H05F 3/00
[52] U.S. Cl. ............. 536/25.3; 205/158; 204/165
[58] Field of Search ............ 536/25.3; 205/158; 204/165

[56] References Cited

FOREIGN PATENT DOCUMENTS 0314009  5/1989  European Pat. Off. .
9108307  6/1991  WIPO .

*Primary Examiner*—Gary L. Kunz
*Attorney, Agent, or Firm*—Oblon, Spivak, McClelland, Maier & Neustadt, P.C.

[57] ABSTRACT

A copolymer of general formula (I),

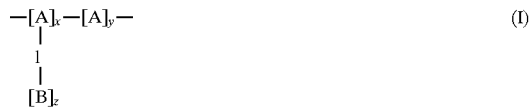

wherein unit A is a monomer of an electronically conductive polymer, unit B is a nucleotide, an oligonucleotide or an analogue thereof, x, y, z are integers of 1 or higher or y is 0, and l is a covalent bond, or a spacer arm. Methods for preparing said polymer and its use, in particular for nucleic acid synthesis, sequencing and hybridization, are also disclosed.

9 Claims, 14 Drawing Sheets

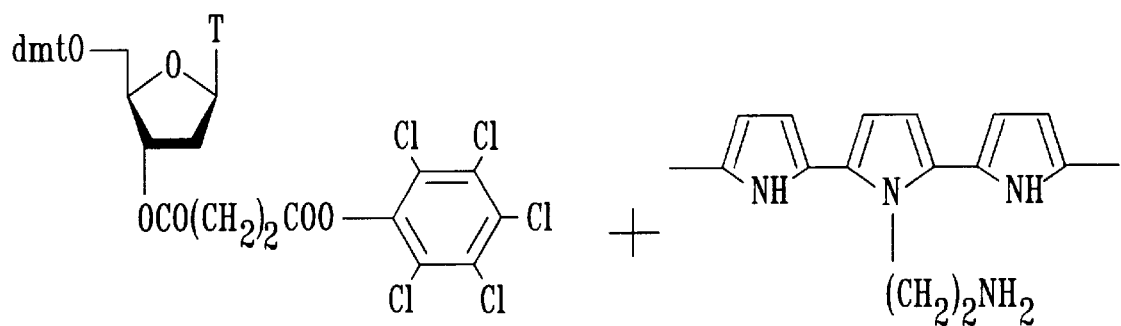
COMPOUND NO. 8
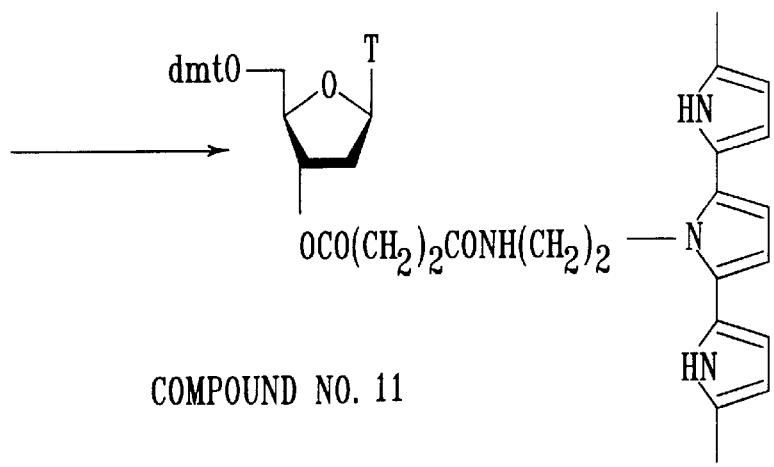
COMPOUND NO. 11
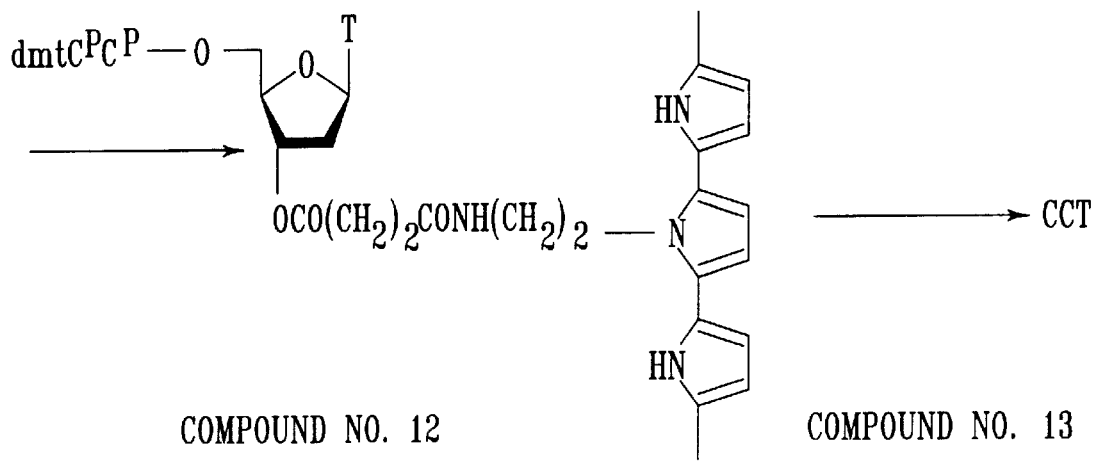
COMPOUND NO. 12  COMPOUND NO. 13
*FIG. 7*

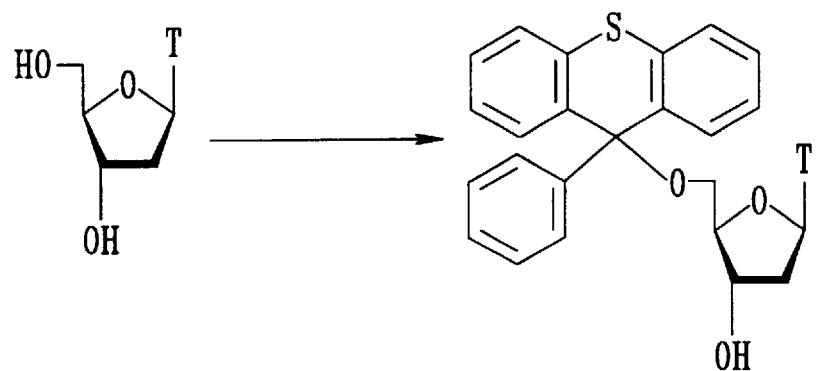
COMPOUND NO. 23
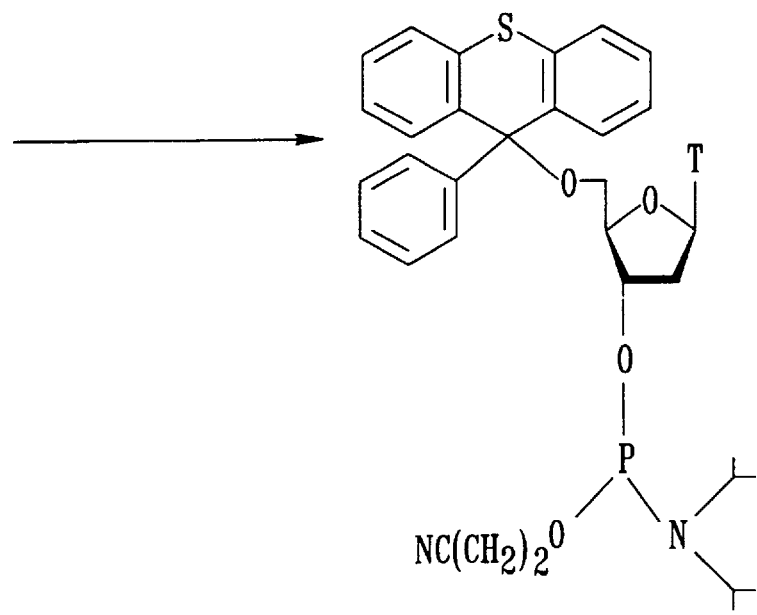
COMPOUND NO. 24
FIG. 14

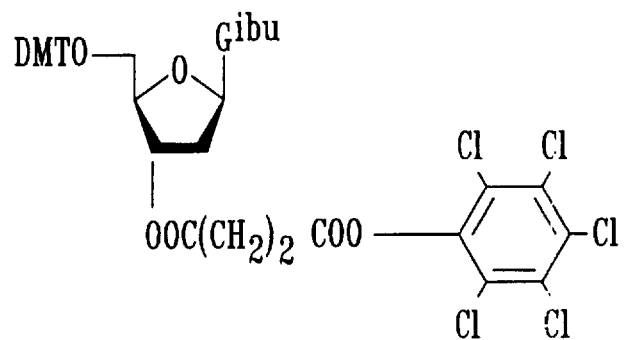
COMPOUND NO. 25
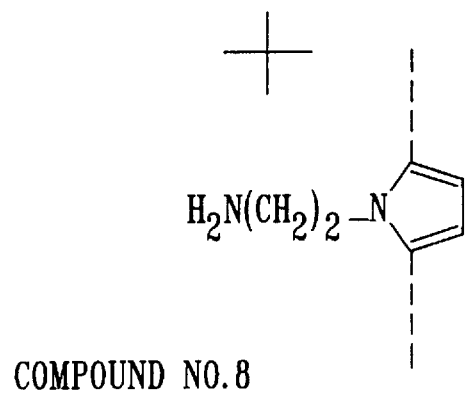
COMPOUND NO. 8
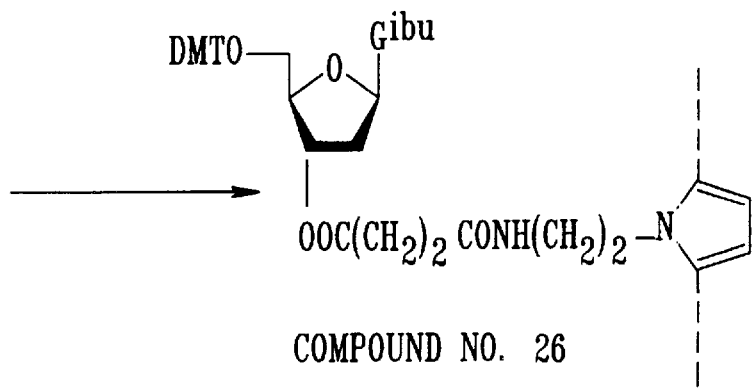
COMPOUND NO. 26
FIG. 15

PREPARATION OF A ELECTRONICALLY CONDUCTIVE POLYMER/NUCLEOTIDE COPOLYMER

This application is the national stage of PCT/FR94/00354 filed Mar. 30, 1994 under 35 USC 371.

The present invention relates to the binding of nucleic acids to an electrically conductive polymer (ECP).

In a great many techniques commonly used in biology, for example the synthesis or hybridization of nucleic acids, oligonucleotides are covalently bound at their end to a solid support. Various supports have been used for this purpose: paper, nylon, glass, silica, polystyrene, polyacrylamide, etc.

At the present time, many teams are researching into the production of supports bearing a large number of oligonucleotides with various sequences, arranged according to a preestablished arrangement, in order simultaneously to perform various reactions (hybridization on a support for example).

Thus, this approach has been proposed, for example, in order to facilitate the sequencing of nucleic acids.

Various oligonucleotides arranged in columns and rows on microsurfaces (oligonucleotide matrices on a support) have been proposed in order to sequence nucleic acids [LYSOV et al., Proc. USSR Acad. Sci., 303, 1508–1511, (1988); KHRAPKO et al., FEBS Lett. 256, 118–122, (1989); KHRAPKO et al., DNA Sequence, vol 1, 375–388 (1991); BAINS & SMITH, J.Theor.Biol. 135, 303–307, (1988); CHURCH & KIEFFER-HIGGINS, Science 240, 185–188 (1988); SOUTHERN, PCT application WO89/10977 (1989)]. The method is based on the hybridization of target DNA or RNA chains on a set of oligonucleotides. In theory, the presence or absence of a sequence in the target nucleic acid may be determined by the hybridization observed on the microsurfaces under defined rigorous conditions.

As regards the in situ synthesis of polynucleotides or polypeptides, by combining the methods of chemical synthesis on a solid phase, photolabile groups and photolithography, FODOR et al. [Science, 251, 767–773 (1991)] have succeeded in synthesizing 1024 peptides on a grid (square, side length 100 μm). These peptides were obtained by simultaneous and parallel syntheses, using photolithography masks and photolabile protecting groups for the peptide synthons. A dCpT dinucleotide was prepared in situ, using thymidine which was 5'-protected by a photolabile protecting group (5'-nitroveratryl thymidine). The light was directed by a photolithography mask and a deposit in a checked pattern with a side length of 100 μm was obtained.

MASKOS & SOUTHERN (Nucleic Acids Res. 1992, 20, 1675–1678) performed, under a microscope, the in situ synthesis of four different oligonucleotides on a glass slide.

Hitherto, the techniques used for the directed deposition of oligonucleotides use either manual deposition (which cannot be used on the industrial scale), or photolithography techniques, which require the use of "masks" and are, moreover, difficult to apply with nucleic acids, which are photolabile.

The aim of the present invention is to obtain novel supports and novel processes for binding oligonucleotides, which do not have the drawbacks of the processes proposed in the prior art.

With this aim, the inventors have had the idea of using electrically conductive polymers as a binding support.

The inventors are now able to bind stably, and via a covalent bond, nucleotides and oligonucleotides to an electrically conductive polymer, and thereby to obtain novel copolymers.

The subject of the present invention is a copolymer which corresponds to the following general formula (I):

in which the unit A represents a monomer of an electrically conductive polymer, the unit B represents a nucleotide, an oligonucleotide or one of the analogues thereof, x, y and z represent integers equal to or greater than 1, or y may be equal to 0, and l represents a covalent bond or a spacer arm.

BRIEF DESCRIPTION OF THE FIGURES

FIG. 7 illustrates the preparation of Compounds No. 8, 11, 12, and 13.

FIG. 14 illustrates the preparation of Compounds 23 and 24.

FIG. 15 illustrates the preparation of Compounds 25, 8, and 26.

Figure 1:
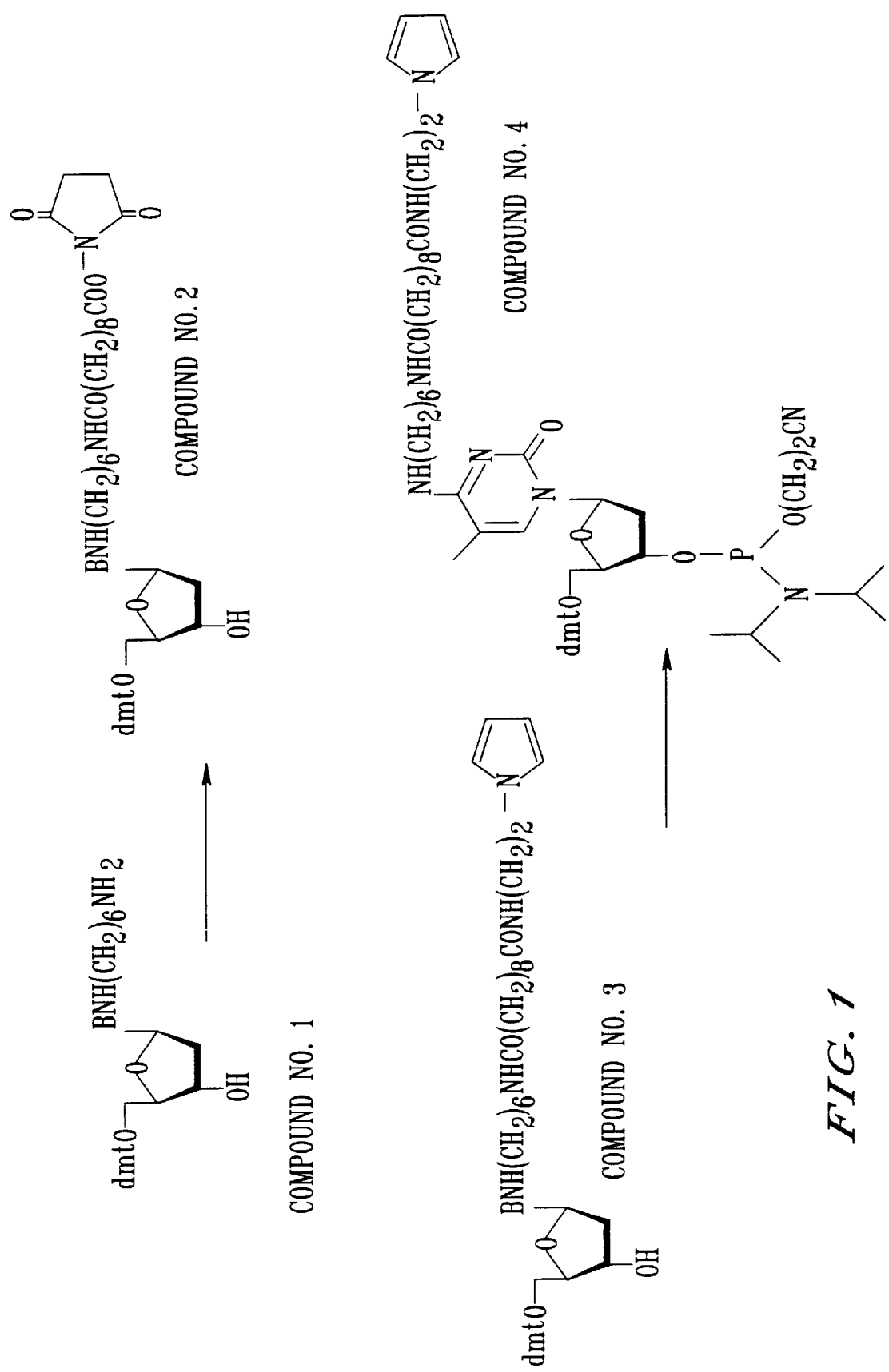
FIG. 1 illustrates the preparation of Compounds No. 1, 2, 3, and 4.

By way of non-limiting example of electrically conductive polymers for which A represents a monomer, polyacetylene, polyazine, poly(p-phenylene), poly(p-phenylene vinylene), polypyrene, polypyrrole, polythiophene, polyfuran, polyselenophene, polypyridazine, polycarbazole, polyaniline, etc. may be mentioned.

A is advantageously a pyrrole unit.

Within the context of the account of the present invention, the term nucleotide analogue is understood to mean any modified nucleotide, such as those described for example by UHLMANN [Chemical Review, 90:4, 543–584 (1990)].

When the unit B is a nucleotide, it may be not only one of those which usually form part of the composition of natural oligonucleotides, but also the analogues or derivatives thereof which are used in the laboratory.

It may be, for example:
* nucleotide analogues forming part of the composition of synthetic oligonucleotides;
* nucleotide derivatives bearing protected functions which are commonly used for the synthesis of nucleic acids; $B_z$ may, in this case, constitute a synthetic intermediate of an oligonucleotide.

$B_z$ may also be an unnatural compound which may hybridize with nucleic acids, such as those described by UHLMANN (abovementioned publication).

The units B forming part of the constitution of $B_z$ may be identical or different, and $B_z$ may constitute a homopolymer or a heteropolymer; in the latter case, the units B may link together in any sequence, which may or may not be predetermined.

According to a preferred embodiment of the present invention, the ratio x/y is between $1/5$ and $1/100,000$.

According to another preferred embodiment of the present invention, l represents a spacer arm corresponding to one of the following formulae:

$$-R_1-[(CH_2)_n-R_2]_x-[(CH_2)_m-R_3]_y-(CH_2)_p-$$

in which:
n is an integer from 1 to 10;
m is equal to 0 or is an integer from 1 to 10;
p is equal to 0 or is an integer from 1 to 10;
x is equal to 0 or is an integer from 1 to 8;
y is equal to 0 or is an integer from 1 to 8;
$R_1$, $R_2$ and $R_3$, which may be identical or different, represent:
$CH_2$; O; S; NR'; CO; CH=CH; NR'CO; CONR'; $NHSO_2$;

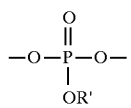

where R' represents a hydrogen atom or a $C_1$ to $C_{12}$ alkyl chain.

The subject of the present invention is the use of an electrically conductive polymer as a support for the binding, via a covalent bond, of at least one nucleotide.

Another subject of the present invention is a process for the preparation of a copolymer of general formula (I).

According to a first variant, this process comprises at least the following steps:
a first step, during which there is prepared a copolymer of general formula (II):

$$-[A^*]_x-[A]_y- \quad (II)$$

in which A, x and y are as defined above, and A* represents functionalized A.

a second step, during which there is bound, to the polymer of formula (II), at least one group of general formula (III):

$$l^*-[B]_z \quad (III)$$

in which B and z are as defined above and l* is an activated arm capable of binding to A*.

In the sense of the present invention, the terms "functionalized" and "activated" are understood to mean the results of any chemical modification whose aim is to provide A and l with chemical functions capable of reacting together to form a covalent bond.

According to another variant, the process for the preparation of the copolymer of general formula (I) comprises at least the following steps:
a step a) during which there is prepared the compound of general formula (IV):

in which A, B, z and l are as defined above,
a step b), during which there is copolymerized the compound (IV) with the monomer A.

Advantageously, at least one step of one or other of the variants of the process in accordance with the invention involves at least one electrochemical reaction. This electrochemical copolymerization is advantageously carried out on an electrode surface; at the end of the reaction, an electrode whose surface consists of a copolymer in accordance with the invention is thereby obtained.

For example, in order to carry out the first variant of the process in accordance with the invention, the step for the preparation of the copolymer of general formula (II) and/or the step for binding of the group of general formula (III) may be carried out by electrochemical reaction; in the second variant, step b) is advantageously carried out by electrochemical copolymerization of the compound (IV) with the monomers A.

The electrochemical copolymerization is, for example, carried out by cyclic voltammetry, by subjecting the mixture [(IV):A] to electrical potential variations which are sufficient to bring about the polymerization by a successive oxidation and reduction; since the polymer formed is conductive, the oxidation-reduction cycle may be repeated several times.

The methods of electrochemical polymerization generally used for the preparation of the ECPs, such as polymerization at set current (chronopotentiometry) or at set potential (chronoamperometry) are also applicable to the preparation of the copolymers in accordance with the invention.

The quality of the deposit may be controlled by the choice of experimental conditions: the oligonucleotide-pyrrole/pyrrole ratio, the bath temperature, the nature of the solvent, the electrochemical method used (cyclic voltammetry, chronoamperometry or chronopotentiometry). The copolymer obtained may accordingly have different qualities of porosity and of accessibility depending on the desired subsequent use, and the amount of bound oligonucleotide may be modified.

Within the context of the implementation of the process in accordance with the invention, the electrochemical reactions are advantageously carried out at the surface of an electrode. By measuring the current delivered during the reaction, the electrode effectively makes it possible to monitor the progress of the polymerization reaction (for example the thickness of the polymer formed) or the progress of subsequent reactions carried out on the copolymer.

According to a preferred embodiment of the process in accordance with the invention in one or other of its variants, it additionally comprises the elongation of the oligonucleotide $B_z$, in several successive steps, each of these steps consisting of the binding of one or more units B.

Elongation of the oligonucleotide $B_z$ is carried out at the surface of the support by assembling the protected monomers, starting with at least one nucleotide or oligonucleotide bound to the surface of the electrically conductive polymer.

The standard methods for the chemical synthesis of nucleic acids may be used in the implementation of this embodiment.

The supports in accordance with the invention additionally allow the oligonucleotide to be elongated electrochemically, by using variations in the electrode potential in order to carry out the protection, deprotection and condensation reactions of the growing polymer chain.

Another subject of the present invention is an electrode, the surface of which consists of a coating comprising a copolymer of formula (I) in accordance with the invention.

Such an electrode may be obtained, for example, by depositing a layer of a copolymer of formula (I) on the surface of an electrode made of platinum, gold, chromium or titanium coated with gold, or vitreous carbon, etc.

Advantageously, several electrodes possibly bearing copolymers of different nature may be combined. A device is thus obtained which may be used for carrying out reactions for the synthesis and/or reactions for the hybridization of nucleic acids.

A particularly advantageous embodiment of a device in accordance with the invention consists in combining several electrodes, at least two of which bear a different group $B_z$. This may, for example, be a set of electrodes in which each bears a different nucleotide (or analogue), or a set of electrodes in which each bears an oligonucleotide of different sequence.

Insofar as it is possible to limit the electrochemical reactions resulting in the binding of the oligonucleotide to a very small surface, a device in accordance with the invention may consist of a plurality of ECP microsurfaces borne by microelectrodes distributed on a support (ECP microchip). In this way, oligonucleotides $B_z$ which may, if so desired, all be different, may be bound in a controlled and organized manner to these microelectrodes.

The "ECP microchip" may in particular be used for sequencing nucleic acids and diagnosis.

By way of non-limiting example illustrating the above, a copolymer [polypyrrole bearing oligonucleotides/polypyrrole] in accordance with the present invention may be obtained:

1) by chemical reaction of a nucleoside, a nucleotide, an oligonucleotide or one of the analogues thereof, with a functionalized polypyrrole. For example, it is possible to carry out the condensation of aminoethylpyrrole with an oligonucleotide bearing a free phosphate or an activated carboxyl at one end.

2) by chemical or electrochemical copolymerization of the pyrrole with the product of condensation of a nucleoside, a nucleotide, an oligonucleotide or one of the analogues thereof, with pyrrole. For example, the pyrrole may be electrochemically copolymerized with an oligonucleotide having a spacer arm bearing a pyrrole at its end. The thickness of the copolymer layer obtained on a platinum surface to which it adheres strongly is from 0.1 $\mu$m to a few $\mu$m, and it may be performed on a surface of 100 $\mu$m$^2$ for example. No interfering degradation reaction of the oligonucleotide could be demonstrated.

3) by preparation of an electrically conductive polymer bearing protected chemical functions. These functions are deprotected locally and selectively in order to allow their coupling with a nucleoside, a nucleotide or an oligonucleotide. For example, it is possible to prepare monomethoxytrityl aminoethyl pyrrole/polypyrrole, and to deprotect it locally either in acidic medium or by applying a potential. The freed amine function may then react with a nucleoside, a nucleotide or an oligonucleotide bearing, for example, an activated phosphate or an activated carboxyl.

4) by stereocontrolled simultaneous synthesis of various oligonucleotides.

The synthesis of an oligonucleotide is carried out at a point on the support by assembling protected nucleotides, starting with a nucleoside which is accessible at the surface of the copolymer. The protected nucleotides may be nucleoside phosphoramidites, nucleoside phosphonates or nucleoside phosphotriesters. Locally, the synthesis is carried out in the same way as an oligonucleotide is synthesized on a silica support in a synthesizer. However, the difference is that the synthesis of the entire set of oligonucleotides is performed simultaneously, by electrochemically performing selective deprotection or condensation operations on a very small surface, thereby making it possible to mask the oligonucleotides which should not react. This allows different oligonucleotides to be synthesized in parallel.

Obviously, the processes briefly outlined above in order to illustrate the synthesis of copolymers [pyrrole/oligonucleotides-pyrrole] are also applicable to polynucleotide analogues, for example analogues of the sugar-phosphate chain such as mono- or dithiophosphates, methylphosphonates and phosphotriesters, and nonionic non-phosphorylated analogues such as formacetals, carbamates and sulfoxides.

The copolymers in accordance with the invention have good stability to mechanical stresses, to moisture, to drying, to heat and to bases, and are thus compatible with a large number of reactions, thereby allowing a wide variety of uses.

The inventors have selectively hybridized oligonucleotides to complementary oligonucleotides bound to a polypyrrole support, and have observed that the use of this support imparts the following advantages:

The copolymer in accordance with the invention is porous, thereby imparting to the oligonucleotides bound to the support a good accessibility for the hybridization with nucleic acids of complementary sequence. This accessibility is demonstrated by the observation of hybridization which is proportional to the thickness of the copolymer layer. A complementary oligonucleotide in the hybridization medium undergoes three times as much hybridization on a pyrrole/oligonucleotide-pyrrole copolymer layer which is three times thicker (and thus contains three times more oligonucleotide bound to the support). The hybridization kinetics are close to those observed with conventional hybridization supports. It should be noted that under the same conditions, a non-complementary oligonucleotide sequence does not bind to the support.

The inventors have also verified that the hybridization is reversible and that any hybridized oligonucleotide may be released by heating, or by treatment with dilute sodium hydroxide, without damaging the polypyrrole and the bound oligonucleotide.

As has been mentioned above, a controlled copolymerization may be performed on extremely small electrode surfaces. This makes it possible to produce a perfectly ordered miniaturized grid on a support, each of the points of this grid bearing an oligonucleotide of fully defined nature. The target nucleic chains bearing a sequence complementary to the chain bound to the support hybridize selectively. This results in an extremely high local density of target nucleic acids, thereby making them easier to detect, or even in certain cases eliminating the need for amplification prior to the detection. The detection of hybridization may in particular be made by means of the electrode which has been used to prepare the copolymer, and which may then be used to measure the association or dissociation phenomena which will take place at the surface thereof. The hybridization of a complementary nucleic acid may, for example, be monitored in situ by an electrical measurement on the electrode which supports the electrically conductive polymer, either by direct measurement, or by labeling the target oligonucleotide with an electroactive molecule such as a phenothiazine or a quinone, for example.

It goes without saying that the traditional methods for detecting the target sequences of nucleic acids are also applicable.

The inventors have additionally succeeded in synthesizing oligonucleotides directly on the copolymer in accordance with the invention by electrochemical deprotection in situ.

In general, the assembly of a nucleotide on a growing polynucleotide chain on a support uses a series of reactions which involve protecting groups in order to direct the reaction onto a given function and to prevent it at another. The inventors have exploited this property in order to direct the reaction for the assembly on the surfaces corresponding to the oligonucleotides chosen where it is desired to insert a nucleotide.

In accordance with the invention, the protecting group for the growing oligonucleotide chain may be removed locally by an electrochemical reaction, thereby making it possible to add a nucleotide to the chosen position.

Additional advantages follow from this possibility of carrying out, on the support in accordance with the invention, an oligonucleotide synthesis in situ. Indeed, in this case, it is possible to synthesize in situ and in parallel the set of oligonucleotides which will be arranged on the grid, instead of independently synthesizing oligonucleotides bearing a pyrrole arm and then carrying out successive copolymerizations. This makes it possible to envisage the industrial production of matrices of several thousand microsurfaces.

The present invention will be better understood with the aid of the remaining description which follows, and which refers to examples for the preparation and use of copolymers in accordance with the invention.

PREPARATION OF A POLYPYRROLE SUPPORT BY COPOLYMERIZATION OF PYRROLE AND OF AN OLIGONUCLEOTIDE BEARING A PYRROLE GROUP: PROPERTIES OF THIS SUPPORT

EXAMPLE No. 1
SYNTHESIS OF MODIFIED OLIGONUCLEOTIDES
I. PREPARATION OF A PYRROLE NUCLEOSIDE AMIDITE
1st METHOD

The overall reaction scheme for this synthesis is illustrated in FIG. 1.

Preparation of Compound No. 1 (FIG. 1)

This compound may be obtained by reacting a diamine with dimethoxytrityl thiothymidine or with dimethoxytrityl thiodeoxyuridine according to the methods described by ROGET et al., [Nucleic Acids Res. 17, 7643–7651 (1989)].

Preparation of Compound No. 2 (FIG. 1)

Compound No. 1 (2 g; 3.1 mmol) is dried by coevaporation with anhydrous acetonitrile and redissolved in 20 ml of dichloromethane. 2 eq of dissuccinimidyl sebacoate (2.45 g; 6.2 mmol) are added. The reaction is left for 3 hours at room temperature. The product obtained is separated on a column of silica (gradient from 0 to 10% of methanol in chloroform) or precipitated in hexane (yield=60%). It may also be used without further purification for the synthesis of Compound No. 3.

Preparation of Compound No. 3 (FIG. 1)

This product is prepared by adding aminoethylpyrrole (1.36 g; 12.4 mmol) to the above reaction mixture or 220 mg of aminoethylpyrrole (2 mmol) to Compound No. 2 obtained after purification. The pH is brought to 8–8.5 by adding a tertiary amine (triethylamine). The reaction is left for 2 hours, and 250 ml of chloroform are added. The organic solution obtained is washed with twice 100 ml of 0.5M $NaHCO_3$, and 100 ml of distilled water, then dried over sodium sulfate. The product is separated on a column of silica with methanol in chloroform (0 to 10%). After evaporation of the solvent, Compound No. 3 is taken up in 10 ml of ethanol and precipitated in 400 ml of ethyl ether (Yield= 60%).

Preparation of Compound No. 4 (FIG. 1)

Compound No. 3 (100 mg; 0.11 mmol) and diisopropylammonium tetrazolate (9 mg; 0.5 eq) are dried by coevaporation in a mixture of anhydrous dichloromethane (2 ml) and anhydrous acetonitrile (3 ml). The residue is taken up in 2.5 ml of dichloromethane stabilized with amylene. Bis (diisopropylaminocyanoethoxy)phosphine (39 µl; 1.2 eq) is added via a septum. After reacting for 2 hours, 20 ml of anhydrous dichloromethane are added. The solution obtained is washed twice with 25 ml of saturated $NaHCO_3$ and then with 25 ml of distilled water. The organic phase is dried over sodium sulfate and evaporated to dryness. The phosphoramidite obtained is taken up in 2 ml of dichloromethane, precipitated in 100 ml of hexane and dried overnight in a desiccator. Compound No. 4 is obtained in a yield of 85%. It is stored under argon at −20° C. in the absence of moisture.

Figure 2:
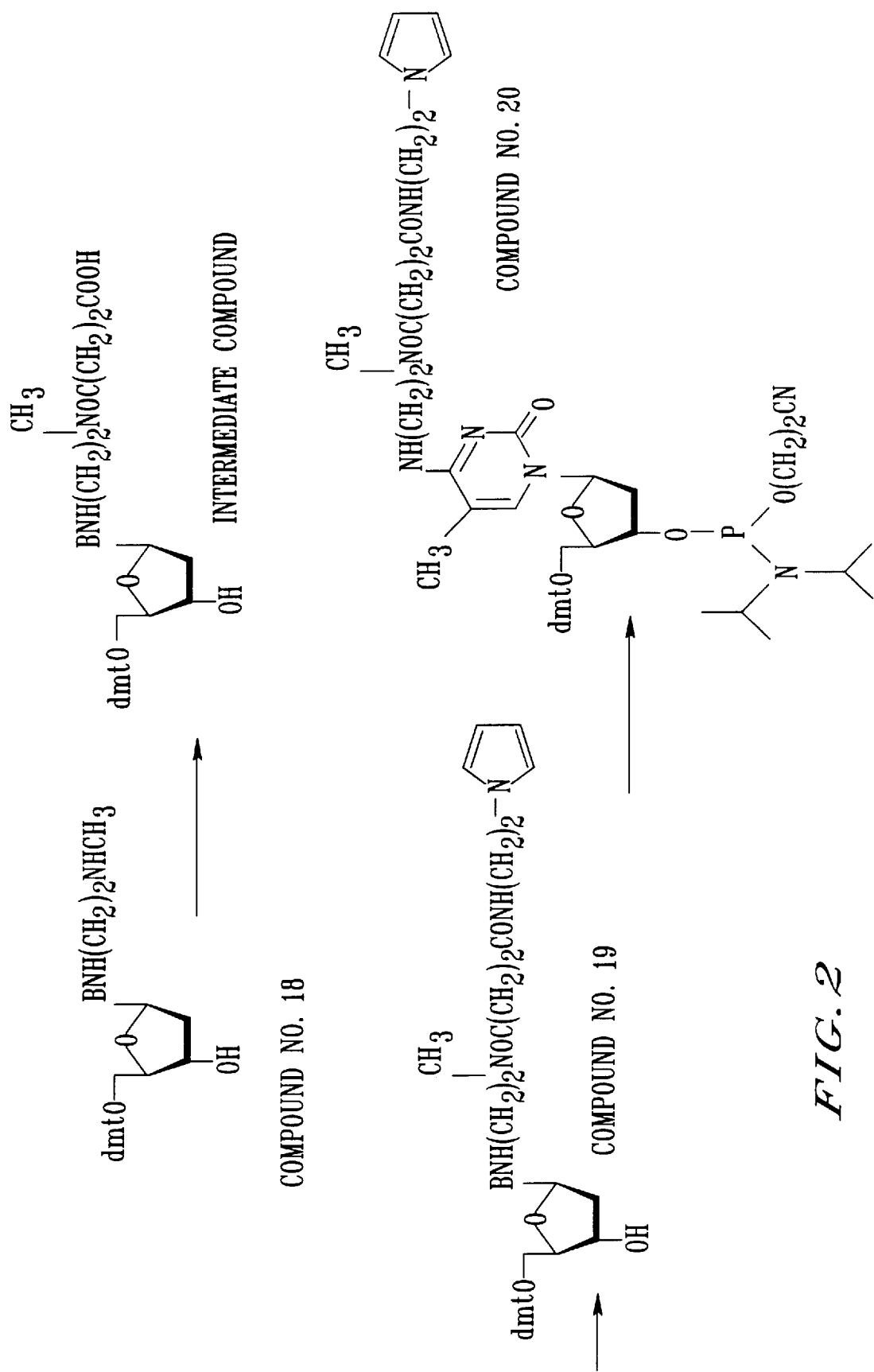
FIG. 2 illustrates the preparation of Compounds No. 18, 19, and 20.

2nd METHOD:

The steps of this process are illustrated in FIG. 2.
PROCEDURE:
Preparation of Compound No. 18 (FIG. 2)

This compound may be prepared by reacting a diamine with dimethoxytrityl thiothymidine or with dimethoxytrityl thiodesoxyuridine according to the methods described by ROGET et al. [Nucleic Acids Res.; 17, 7643–7651 (1989)].

Preparation of Compound No. 19 (FIG. 2)

Compound No. 18 (4 g; 6.60 mmol) is dried by coevaporation in anhydrous pyridine and is redissolved in 4 ml of anhydrous pyridine and 40 ml of anhydrous THF (tetrahydrofuran).

1.2 eq of succinic anhydride (800 mg; 8 mmol) are added, and the mixture is left to react for 1 h. The solvents are evaporated off and, in order to remove the pyridine, the mixture is then coevaporated with toluene. 1.5 eq of aminoethylpyrrole (1.1 ml; 9.9 mmol) are added. The mixture is coevaporated with THF. 30 ml of THF and 2 eq of DCC (dicyclohexylcarbodiimide) (2.70 g; 13.2 mmol), predissolved in 30 ml of THF, are added. The reaction is left overnight. The precipitate is removed by filtration and washed with dichloromethane until it is white. The filtrate is evaporated to dryness and taken up in 250 ml of dichloromethane. The organic solution obtained is washed with 2×250 ml of saturated $NaHCO_3$ and then with 250 ml of distilled water. The organic phase is dried over sodium sulfate and evaporated to dryness. The product (Compound No. 19) is purified by chromatography on a column of silica. It is eluted with $CH_2Cl_2$/MeOH/TEA: 97.5/2.5/1. Yield= 67%.

Preparation of Compound No. 20 (FIG. 2)

Compound No. 19 (600 mg; 0.75 mmol) and diisopropylammonium tetrazolate (63 mg; 0.37 mmol) are dried by coevaporation in dichloromethane/acetonitrile: 2.5 ml/2.5 ml, and then taken up in 5 ml of dichloromethane. Bis (diisopropylaminocyanoethoxyphos-phine (280 µl; 0.9 mmol) is added via a septum. After reacting for 2 hours, 20 ml of dichloromethane are added. The organic solution obtained is washed with 2×25 ml of saturated $NaHCO_3$ and then with 25 ml of saturated NaCl. The organic phase is dried over $Na_2SO_4$ and evaporated to dryness. The evaporation residue is taken up in 5 ml of dichloromethane. The product (Compound No. 20) is obtained by precipitation in hexane, in a yield of 78%. After drying overnight in a desiccator under vacuum, it is stored under argon at −20° C. in the absence of moisture.

II. PREPARATION OF A PYRROLE NUCLEOSIDE

Preparation of Compound No. 5

Compound No. 4 (68 mg; 0.06 mmol) is redissolved in 300 µl of anhydrous acetonitrile (0.2M solution). This product is used to prepare an oligonucleotide (Oligo-1-pyr) of sequence Pyr-TGT ACC TGA ATC GTC CGC CAT, in which Pyr represents the nucleotide derivative corresponding to Compound No. 4. This oligonucleotide is prepared on an automatic DNA synthesizer (Applied Biosystems 381A) according to the procedures described by the manufacturer. Compound No. 4 of the invention is subjected to the same synthetic cycle as the normal phosphoramidites (A C G T). Only the concentration (0.2M instead of 0.1M) and the reaction time (30 seconds instead of 15 seconds) are increased for Compound No. 4.

After synthesis, the oligonucleotide-pyrrole is detritylated on the support, by the action of 3% TCA (trichloroacetic acid). It is cleaved from the support with 4×500 µl of 28% $NH_4OH$. Heating of this solution for 16 hours at 60° C. allows the protecting groups to be removed. Compound No. 5 (represented in FIG. 3) is obtained by reverse phase chromatography using a gradient of 10 to 50% of acetonitrile in triethylammonium acetate (25 mM, pH 7).

Compound No. 20 may be used in the same way as Compound No. 4.

EXAMPLE 2

Figure 3:
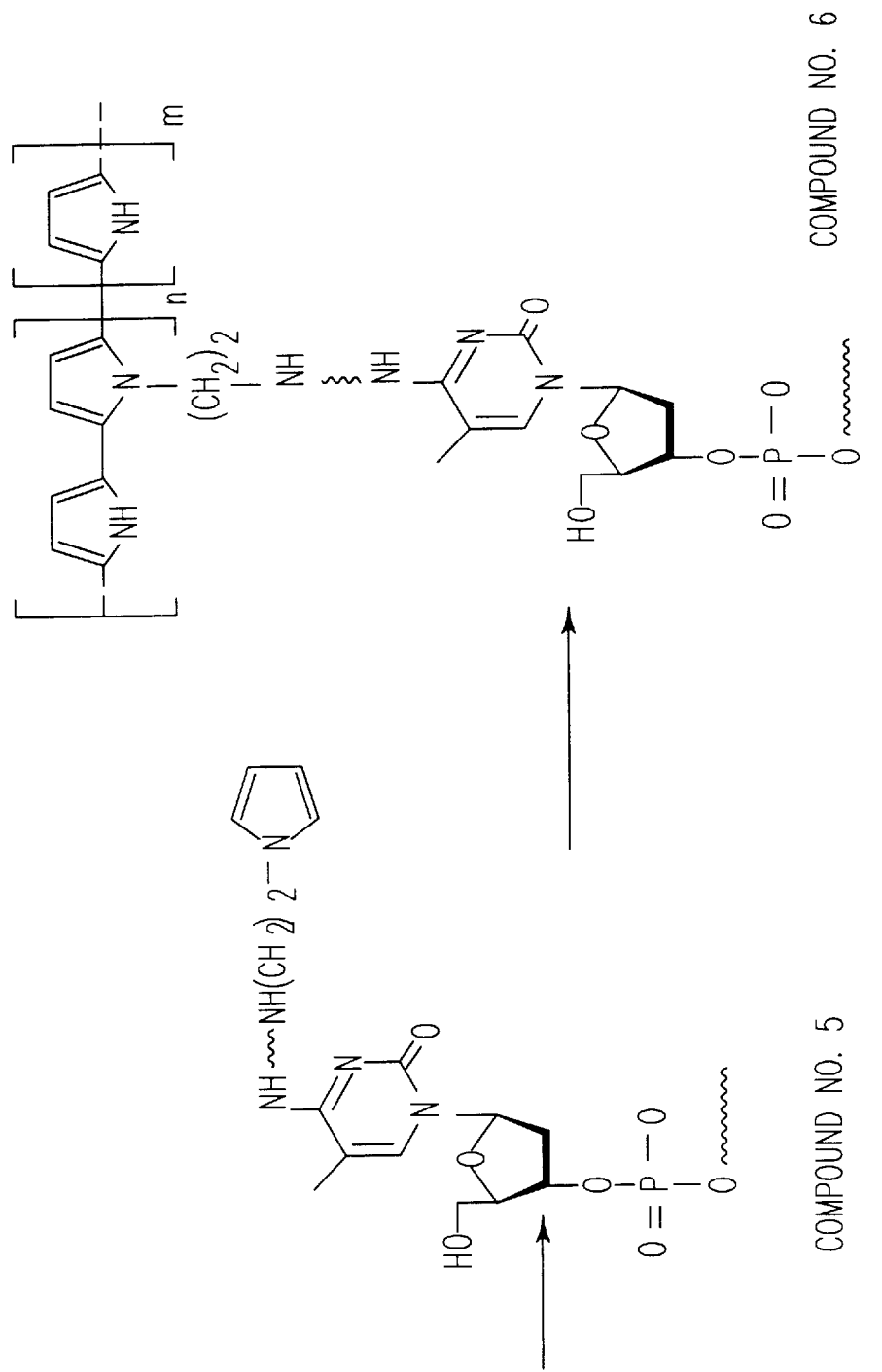
FIG. 3 illustrates the preparation of Compounds No. 5 and 6.

PREPARATION OF THE ECP-POLYNUCLEOTIDE SUPPORT BY ELECTRO-COPOLYMERIZATION (Compound No. 6, FIG. 3)

A—Principle of the technique

Figure 4A:
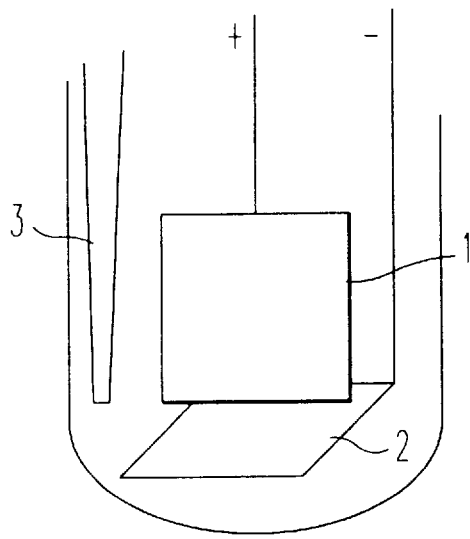
FIGS. 4A and 4B show a schematic representation of an electropolymerization cell (A) and cyclic voltammetry curves (intensity as a function of the potential) over 12 polymerization cycles (B).

Oxidized pyrrole rings are capable of polymerizing to form an insoluble polymer, polypyrrole. An electropolymerization cell is represented schematically in FIG. 4a: this cell comprises a working electrode (1), a counterelectrode (2) and a reference electrode (3).

If the oxidation is performed electrochemically, the polypyrrole will only be synthesized on the working electrode. This thus allows a very localized synthesis of a polymer. An oligonucleotide bearing a pyrrole ring at the end of one arm may thus be inserted into the polymer simply by copolymerizing the pyrroles. The desired polymer is thus obtained (Compound No. 6, FIG. 3).

Since the polymer formed (polypyrrole) is conductive, these reactions may be continued and several synthetic cycles may be performed (there is only a variation in the resistance of the electrode at each cycle).

B—Method

The polymerization is carried out on a platinum electrode 60 $mm^2$ in a solution containing $10^{-2}$M pyrrole, $5.10^{-7}$M substituted pyrrole, oligonucleotide bearing a 5' pyrrole group (Oligo-1-pyr) and 0.1 M $LiClO_4$ (doping agent).

The oligonucleotide bearing the 5' pyrrole (Compound No. 5, Oligo-1-pyr) was synthesized according to the method described above in Example 1, and purified by reverse phase HPLC. An oligonucleotide of the same sequence (Oligo-1) not bearing pyrrole served as a negative control.

These two products were 5'-labeled with $^{32}$p in order for the copolymerization reactions to be monitored more easily.

Figure 4B:
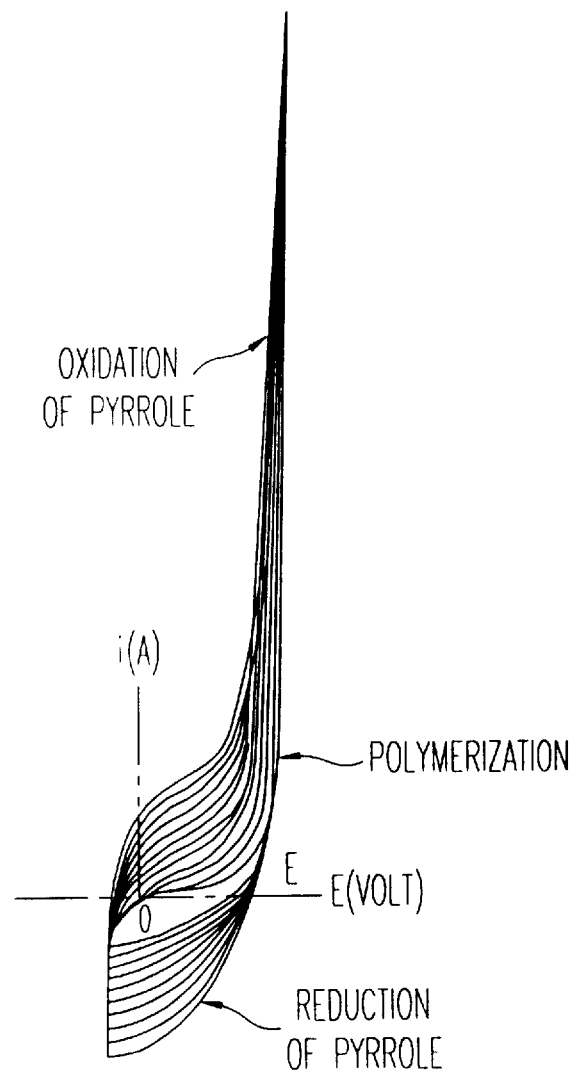

The reactions for the oxidation of the monomer and for the reduction of the polymer are provided for by a cyclic variation of the potential between −0.4 and +0.9 V/ECS. FIG. 4b represents the cyclic voltammetry curves (intensity as a function of the potential) over 12 polymerization cycles.

Integration of the current with respect to time (amount of electrons consumed) allows an evaluation of the mass of polymer formed on the surface of the electrode and thus the thickness of the film (of the order of 0.2 µm for $5.10^{-2}$ C).

C—Results

* Stability of an oligonucleotide under the electropolymerization conditions

Checking by HPLC of the oligonucleotide in solution subjected to the electropolymerization shows no degradation of the latter.

* Actual migration of an oligonucleotide subjected to a potential

A nucleic acid is a polyanionic molecule capable of migrating in an electric field; however, owing to the presence of perchlorate ions in the medium, no migration is observed. Moreover, no adsorption of the oligonucleotides onto a preformed polypyrrole can be measured.

* Specificity and level of incorporation of oligonucleotides during the copolymerization 1—Polymerization of the pyrrole is carried out in the presence of the unmodified oligonucleotide 1 oligo-1 (TGT ACC TGA ATC GTC CGC CAT) (SEQ ID NO:1).

Oligo-1 : $10^{-9}$M in the reaction medium

Oligo-1 on support : $4.10^{-12}$ mol, i.e. 0.4% of nonspecific incorporation.

2—The polymerization is carried out in the presence of the modified oligonucleotide Oligo-1-pyr (P TGT ACC TGA ATC GTC CGC CAT)

Oligo-1-pyr : $10^{-9}$M in the reaction medium

Oligo-1-pyr on support : $7.2.10^{-12}$ mol, i.e. 0.72% incorporation.

44% of the oligonucleotides-pyrroles detected on the support are effffectively bound by the pyrrole group. However, by adding 0.2M thymidine 5'phosphate to the electropolymerization solution, the specificity of anchoring then increases to 80%, by decreasing the binding of the non-modified oligonucleotide.

* Electrochemical reactivity of the oligonucleotide-pyrrole

The starting solution contains 1 oligonucleotide-pyrrole per 20,000 pyrrole monomers. By calculating the mass of the polymer formed and the amount of oligonucleotide bound, it is estimated that the polymer comprises 1 oligonucleotide-pyrrole per 60,000 pyrrole chain units.

Oligonucleotide-pyrrole is thus incorporated 3 times less than a free pyrrole, thereby constituting an entirely satisfactory level of incorporation.

* Density of binding

Under the experimental conditions outlined above, 5.3 pmol/$cm^2$ of oligonucleotides are bound.

The proportion of oligonucleotide integrated into the polymer (1/60,000) may readily be improved by increasing the [oligonucleotide-pyrrole/pyrrole monomer] ratio in the reaction medium. This may be achieved in three different ways:

increasing the amount of oligonucleotide;

decreasing the concentration of free pyrrole;

decreasing the reaction volume.

EXAMPLE 3
PROPERTIES OF THE OLIGONUCLEOTIDE-POLYPYRROLE COPOLYMERS IN ACCORDANCE WITH THE INVENTION: USE OF NUCLEIC ACIDS AS A HYBRIDIZATION SUPPORT

A polypyrrole support bearing the oligonucleotide Oligo-1 was synthesized according to the method described in Example 2. The electropolymerization was carried out up to charges of $5 \times 10^{-2}$ C in order to obtain a support 0.2 μm in thickness, and of $15 \times 10^{-2}$ C in order to obtain a support 0.6 μm in thickness. The hybridization reactions are carried out in a 20 mM phosphate buffer pH 7.4, 300 mM NaCl, 0.5% SDS. The washes are performed in the same buffer but which is diluted 4-fold. All these reactions are carried out at room temperature.

Results

The accessibility of the grafted oligonucleotides was verified by their capacity to hybridize with a $^{32}$P-labeled complementary oligonucleotide in the surrounding liquid medium.

a) Hybridization

Figure 5:
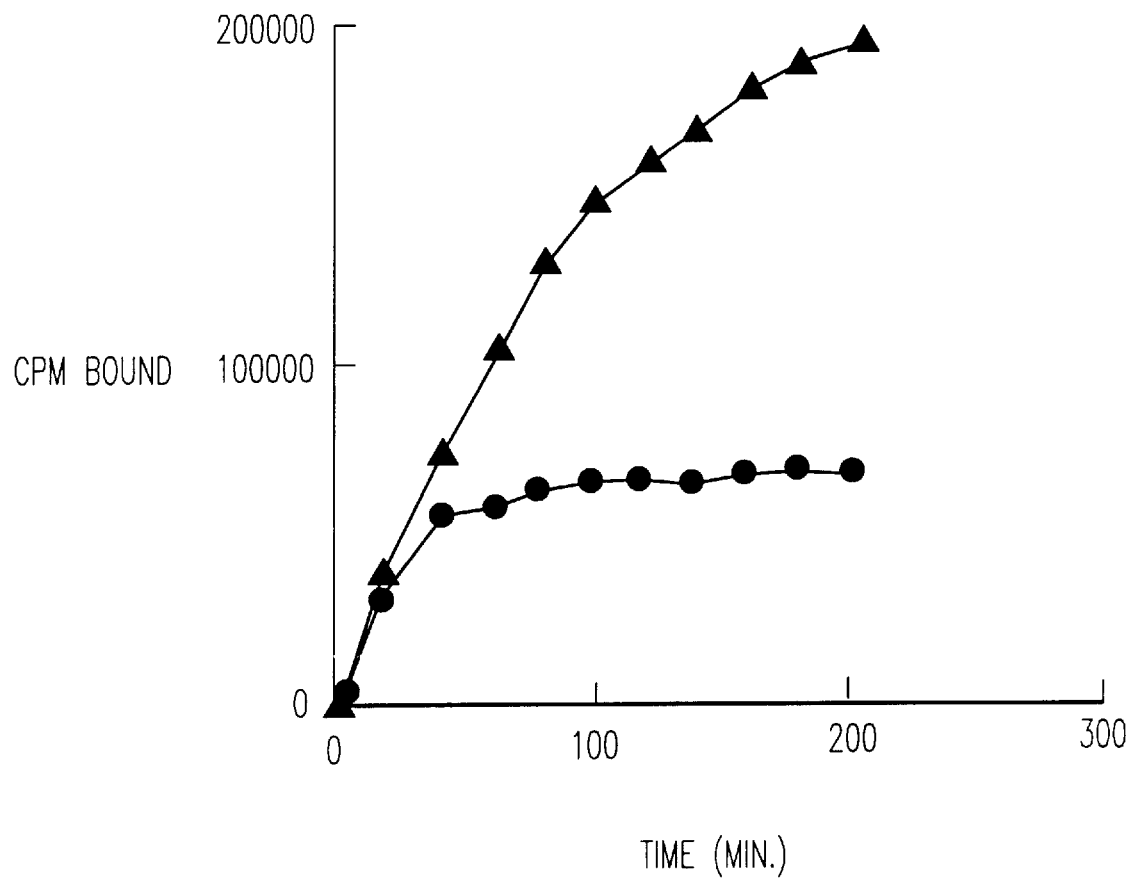
FIG. 5 shows the kinetics of hybridization to supports of differing thickness.

The kinetics for the hybridization of the supports of various thicknesses is comparable, and the total hybridization capacity is proportional to the thickness of the support, as shown in FIG. 5, which represents on the x axis the hybridization time (in minutes) and on the y axis the amount of $^{32}$P-labeled complementary oligonucleotide bound to the support (in cpm), for two different thicknesses: (●)=support 0.2 μm in thickness; (▲)=support 0.6 μm in thickness.

b) Denaturation

Figure 6A:
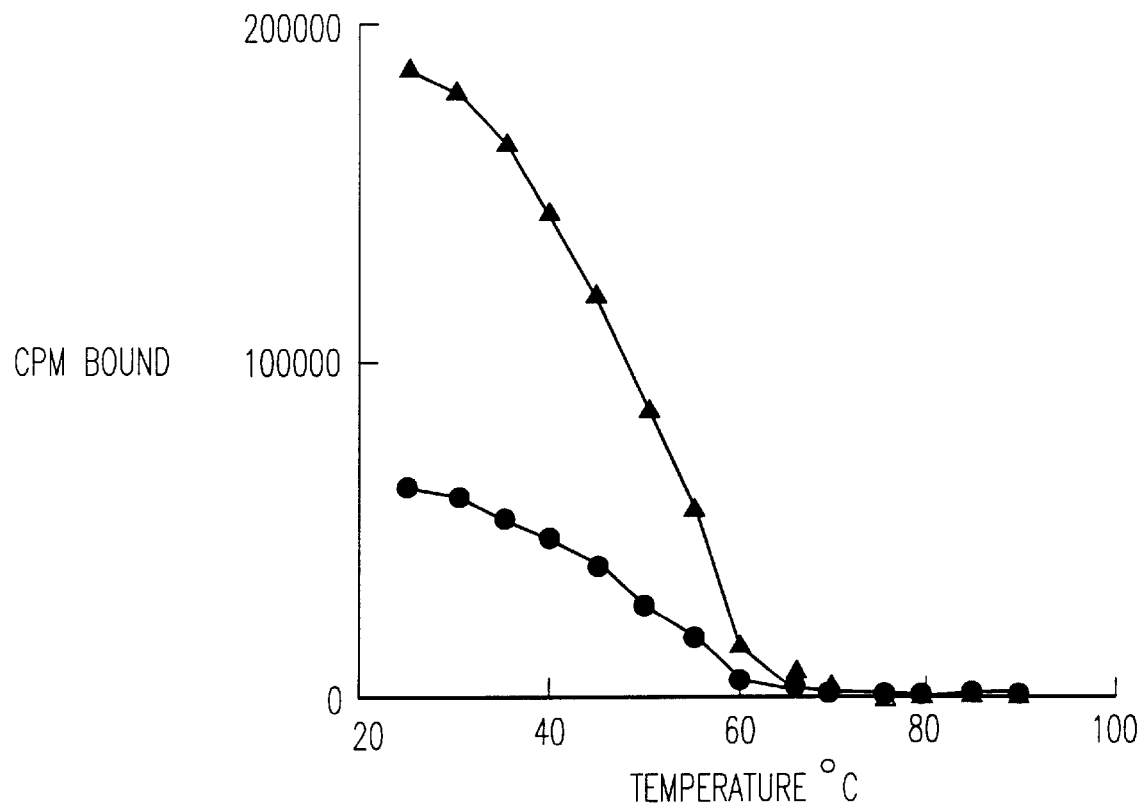
FIGS. 6A and 6B show the amount of oligonucleotides remaining on the electrode (A) and the rate of denaturation as a function of the washing temperature.
Figure 6B:
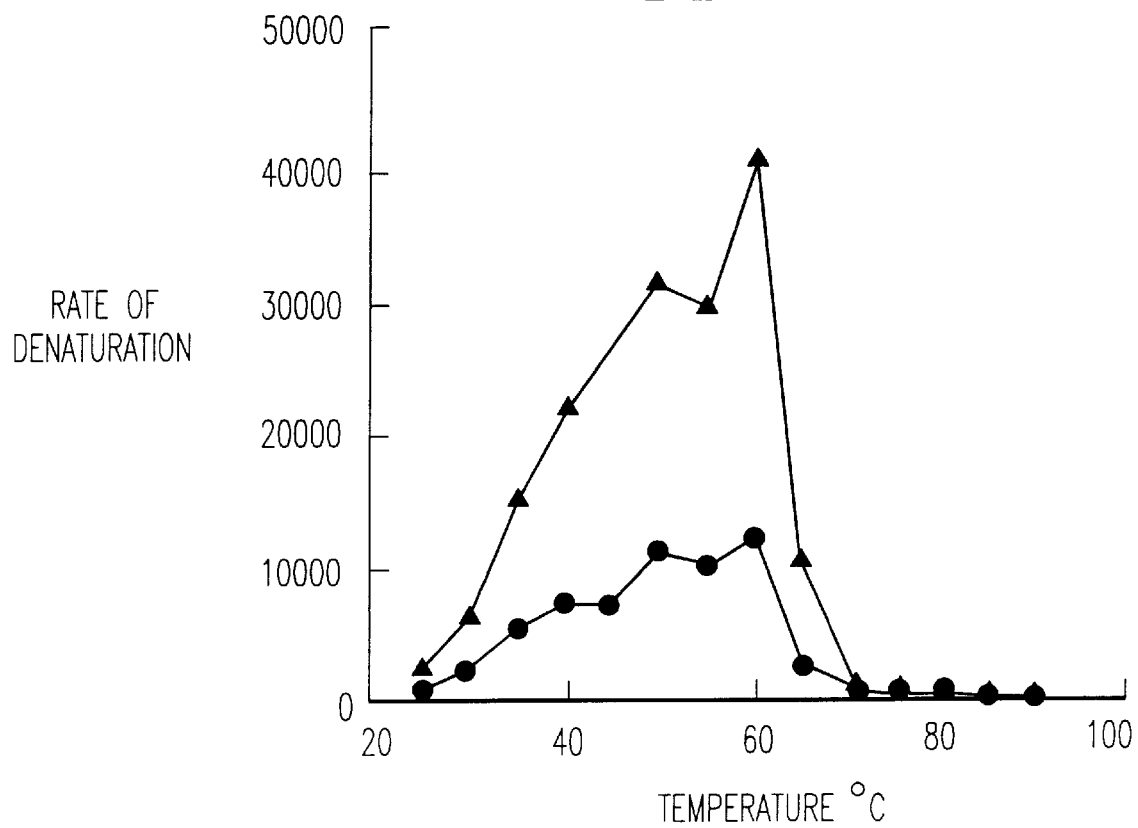

It is possible to monitor the duplex denaturation continuously, thereby revealing the reversibility of the hybridization phenomenon. FIGS. 6a and 6b respectively illustrate the amount of oligonucleotides remaining on the electrode and the rate of denaturation as a function of the washing temperature (for a temperature variation of 1° C. per minute) on the supports of different thickness: (●): 0.2 μm; (▲)=0.6 μm.

Moreover, it has been verified that the oligonucleotide-polypyrrole support is not affected by denaturation/renaturation cycles.

Under the experimental conditions used, the maximum rate of denaturation is achieved at about 60° C., which corresponds to the theoretical melting point of the oligonucleotide (61.5° C.).

EXAMPLE No. 4
SYNTHESIS IN SITU OF OLIGONUCLEOTIDES ON A POLYPYRROLE SUPPORT

I.—BINDING OF THE 1st NUCLEOTIDE

1st METHOD

Preparation of Compound No. 13

The reaction scheme is illustrated by FIG. 7.

The support (Compound No. 8, FIG. 7) is prepared by electropolymerization of a solution of pyrrole and aminoethylpyrrole ($10^{-2}$M/$10^{-3}$M) in the presence of 0.1M LiClO$_4$ in acetonitrile. The electropolymerization takes place by sweeping from −0.3 V to +0.85 V relative to $10^{-2}$ M Ag/Ag+ on a 60 mm$^2$ platinum electrode.

Preparation of Compound No. 11 (FIG. 7)

Compound No. 8 is washed with anhydrous acetonitrile (2×5 ml) and then with triethylamine in acetonitrile (500 μl/5 ml).

10 mg of activated nucleoside (Compound No. 2) are dried by coevaporation in anhydrous acetonitrile, taken up in 500 μl of anhydrous acetonitrile and added to the support in a hermetically stoppered flask. The mixture is placed under gentle mechanical agitation for 24 hours. The support is removed and washed with acetonitrile and then with dichloromethane until the color of the trityl has disappeared in the washing solvents.

The amine functions of the support which have not reacted with the nucleoside have to be blocked. This has been carried out by "capping" with an acetic anhydride/N-methylimidazole mixture in pyridine. The reaction is left for 6 hours. The functionalized support (Compound No. 11) is then washed thoroughly with 3×10 ml of pyridine, 3×10 ml of acetonitrile and 3×10 ml of dichloromethane successively.

2nd METHOD

Figure 8:
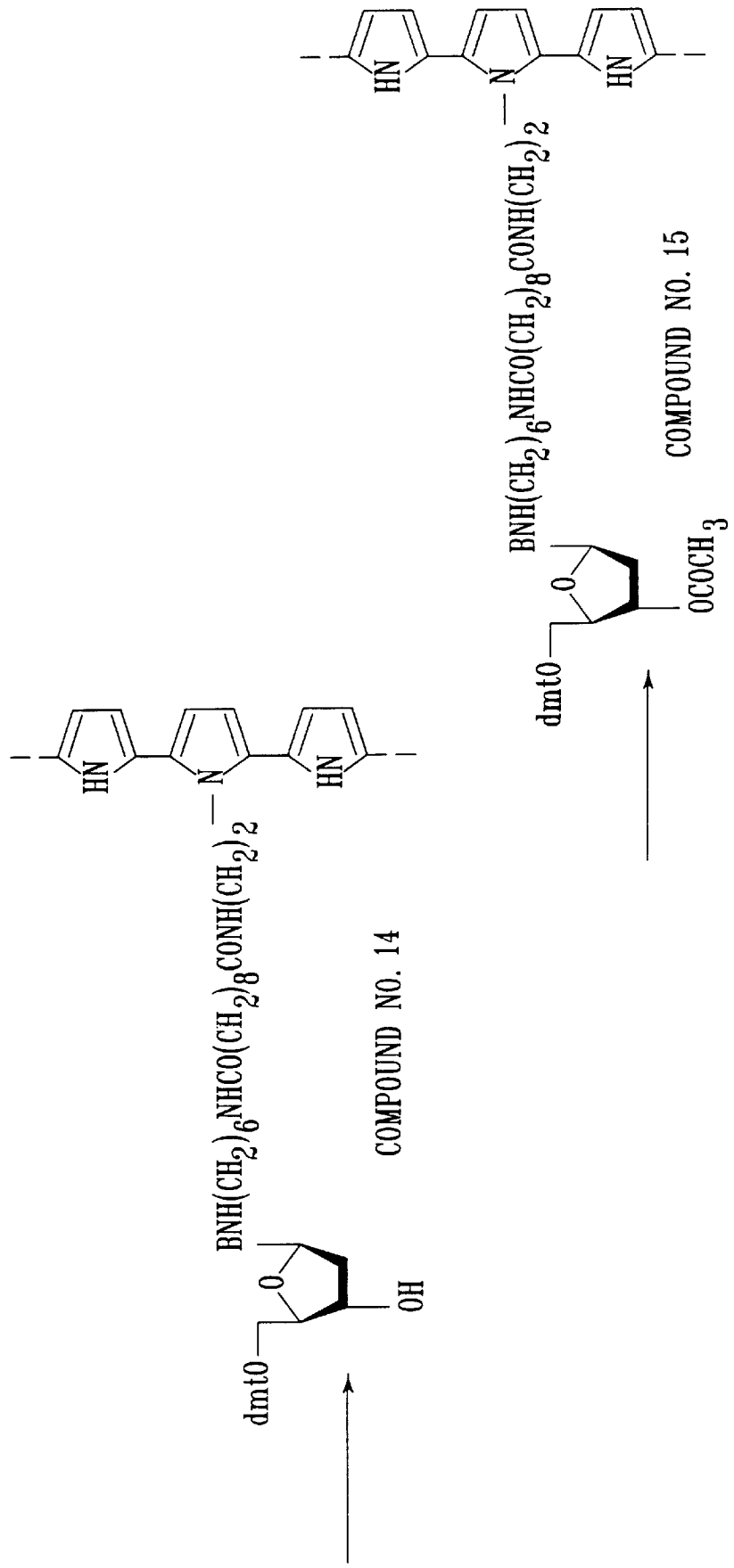
FIG. 8 illustrates the preparation of Compounds No. 14 and 15.

The reaction scheme is illustrated in FIG. 8.

Preparation of Compound No. 14 (FIG. 8)

The amino polypyrrole (Compound No. 8) is washed with anhydrous acetonitrile (2×5 ml) and then with triethylamine in acetonitrile (500 μl/5 ml). The activated nucleoside (Compound No. 2) (20 mg) is dried by coevaporation in anhydrous acetonitrile, then taken up in 1 ml of anhydrous acetonitrile and added to the support (Compound No. 8) in a hermetically stoppered flask. The mixture is placed under gentle mechanical agitation for 24 hours. The grafted support (Compound No. 14) is washed with acetonitrile and then with dichloromethane until the color of the trityl has disappeared in the washing solvents during their acidification.

Preparation of Compound No. 15 (FIG. 8)

The secondary alcohol functions provided by the nucleoside and the amine functions of the support which have not reacted must be masked. For this, blocking is performed with an acetic anhydride/N-methylimidazole mixture in pyridine (1 ml) for 6 hours. Washing with pyridine (2×5 ml), acetonitrile (2×5 ml) and dichloromethane (2×5 ml) allows Compound No. 15 to be obtained.

II.—ELONGATION OF THE OLIGONUCLEOTIDE

Preparation of Compound No. 12 (FIG. 7)

The trimer d(CCT) was prepared on a platinum electrode coated with polypyrrole, by two methods:

synthesis with chemical deprotection, according to the usual cycle of the phosphoramidite synthesis, synthesis with electrochemical detritylation.

a) Chemical synthesis

Figure 9:
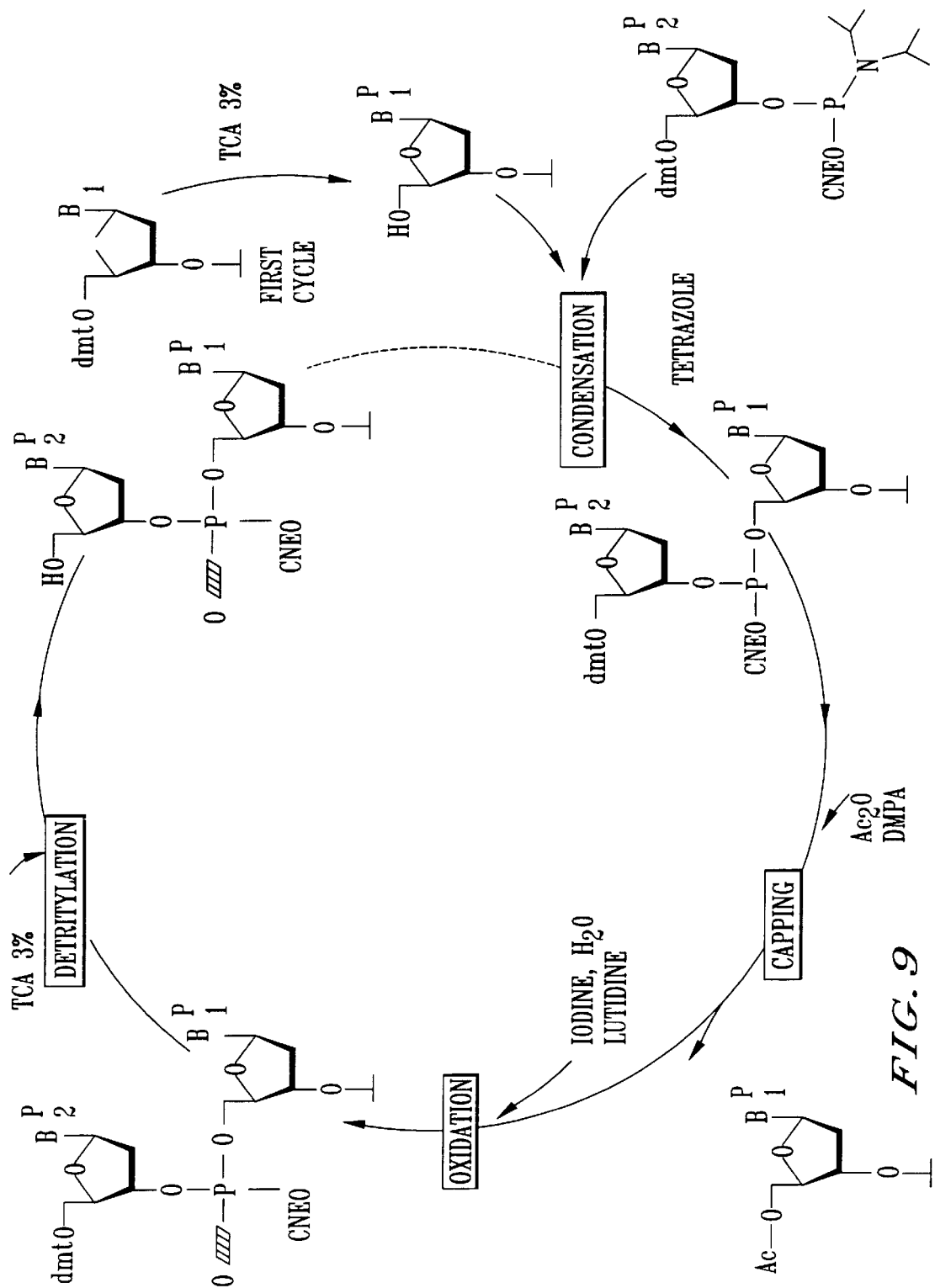
FIG. 9 illustrates the chemical synthesis of oligonucleotides.

The following steps are carried out, as many times as necessary, each step corresponding to the binding of a nucleotide; these steps are represented in FIG. 9:

detritylation of the support with 4×500 μl of 2% trichloroacetic acid in dichloromethane;

rinsing with acetonitrile in order to remove the reagent (5×1 ml);

washing with anhydrous acetonitrile for DNA synthesis (3×1 ml);

addition of 250 μl of 0.1M phosphoramidite and 250 μl of 0.5M tetrazole;

coupling (2 min) and removal of the nucleoside solution;

rinsing with acetonitrile (5×1 ml);

acetic anhydride/methylimidazole capping (500 μl, 1 min);

rinsing with acetonitrile (2×1 ml);

oxidation with iodine/lutidine 1 min (500 μl, 1 min);

rinsing with 5×1 ml of acetonitrile;

detritylation, and start of a new cycle, etc.

Measurement of the trityls after each cycle respectively gives: 0.090 OD/2 ml (dT), 0.095 OD/2 ml (dCT) and 0.087 OD/2 ml (dCCT).

b) Synthesis with electrochemical deprotection

The synthesis steps are the same as for the chemical synthesis above, but the detritylation is performed by application of a potential of 1.2 V for 5 min.

The detritylation cannot be quantified since the trityl cation formed is captured by the anode, which subtracts it from the measurement. The coupling cycle was, however, performed.

Preparation of Compound No. 13 (FIG. 7)

Cleavage of the support and removal of the protecting groups are done with 2 ml of aqueous ammonia in a glass tube closed with a screw-thread stopper, and the reaction is carried out for 48 hours at room temperature.

The controls prepared on a silica column are deprotected with 4×250 µl of aqueous ammonia in order to detach them from the support (t=4×½ h). The ammonia solution is then left for 48 hours at room temperature. The solutions are evaporated and analyzed by reverse phase chromatography on a 5 µm by 25 cm C4 column. A gradient of 0 to 30% of B (25 mM triethylammonium acetate, pH 7 and 50% acetonitrile) in A (25 mM triethylammonium acetate, pH 7) is applied over 30 min.

Figure 10:
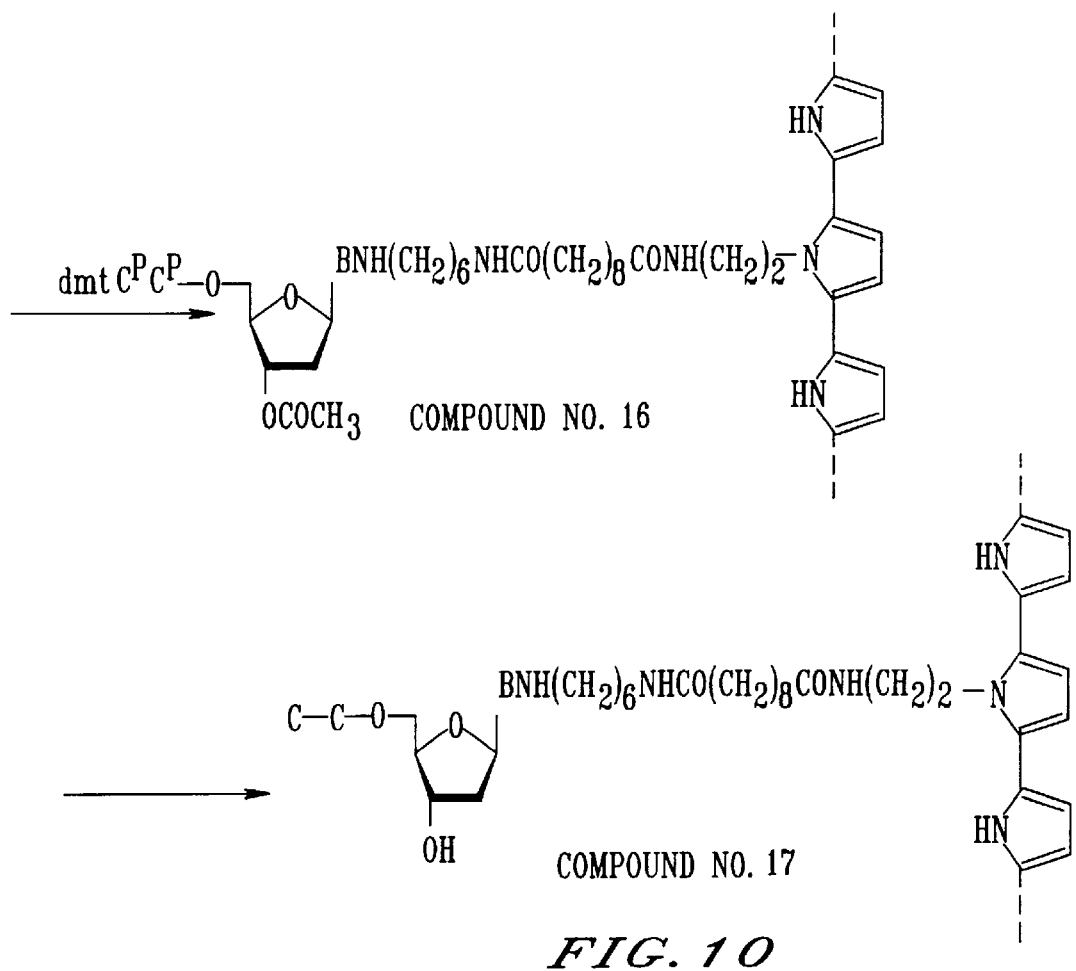
FIG. 10 illustrates the preparation of Compound No. 16 and 17.

Preparation of Compound No. 16 (FIG. 10)

Compound No. 16 is synthesized according to the same procedure as Compound No. 12, with similar results for the detritylation. This shows that the nature of the spacer arm has little influence on the chemical synthesis.

Preparation of Compound No. 17 (FIG. 10)

Compound No. 16 is deprotected for 48 hours at room temperature in 28% aqueous ammonia in a hermetically stoppered flask. The dimethoxytrityl group is then cleaved with 3% trichloroacetic acid (3×3 ml) and measured in order to verify that the oligonucleotide is still on the support.

EXAMPLE NO. 5
OLIGONUCLEOTIDES-PYRROLE COPOLYMERIZATION ON MICROELECTRODES

Figure 11A:
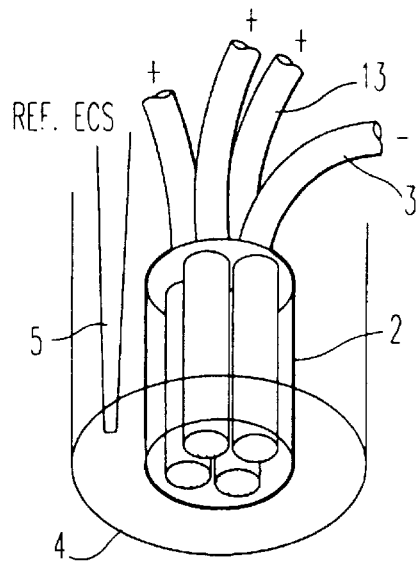
FIGS. 11A and 11B show a matrix of four electrodes (A) and voltammagrams during polymerization (B).

A matrix of four electrodes represented in FIG. 11a is made by insertion of four platinum wires (1) (diameter 0.6 mm) into a glass cylinder (2) (diameter 5 mm×height 10 mm). One of the electrodes is used as counter-electrode (3). This matrix system makes it possible to bind various oligonucleotides to each point of the matrix.

The electrode matrix is placed inside a container (4) in which the reaction is carried out, and in which a reference electrode (5) is also immersed.

The 3 working electrodes are successively electrochemically coated with a copolymer composed of pyrrole and of oligonucleotides capable of detecting, by hybridization, a mutation in codon 61 of the human ras H gene. These 3 oligonucleotides bearing a 5' pyrrole group are as follows:
normal oligo: 5' Pyr TCCTCCTGGCCGG 3'(SEQ ID NO:2)
A-mutated oligo: 5' Pyr TCCTCCAGGCCGG 3'(SEQ ID NO:3)
C-mutated oligo: 5' Pyr TCCTCCCGGCCGG 3'(SEQ ID NO:4)

Each oligonucleotide is successively copolymerized on each electrode under the conditions described in Example 2, but in a reaction volume of 300 µl instead of 3 ml.

Figure 11B:
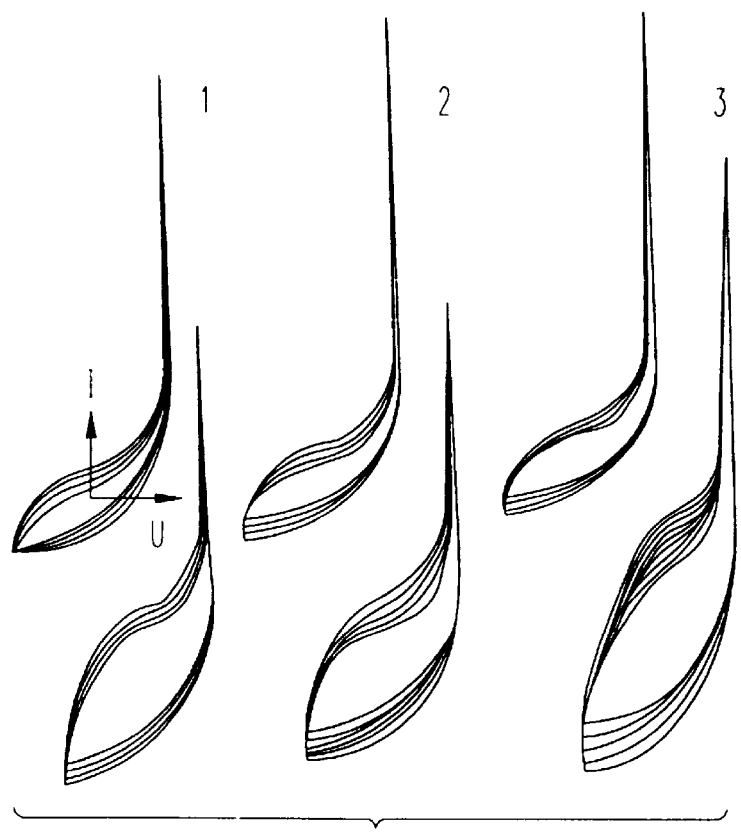

The voltammagrams obtained are represented in FIG. 11b: ((1) polymerization on the first electrode; (2) polymerization on the second electrode; (3) polymerization on the third electrode). These voltammagrams are very uniform and very reproducible both at reduced charge (2 to $4×10^{-4}$ C, top curves) and at high charge (1 to $1.3×10^{-3}$ C, bottom curves). Under these conditions, $6×10^{-14}$ mol of oligonucleotide are bound on 0.3 mm$^2$ (i.e. 18 pmol/cm$^2$) for a film thickness of 0.1 µm (charge of $10^{-4}$ C).

Detection of a bridging mutation of a nucleic acid by hybridization on a 3-point matrix Three nucleic acid fragments 51 nucleotides in length are used in order to simulate the desired natural ras H mutations.

These three nucleic acids have the sequence:
normal ras H (SEQ ID NO:5): 5' CTGTTGGACATCCTG-GATGCCGGCCAGGAGGAGTACAGCGC-CATGCGCGAC 3'
T-mutated ras H (SEQ ID NO: 6): 5' CTGTTGGACATC-CTGGATGCCGGCCTGGAGGAGTA-CAGCGCCATGCGCGAC 3'
G-mutated ras H 5' CTGTTGGACATCCTGGATGCCG-GCCGGGAGGAGTACAGCGCCATGCGCGAC 3'(SEQ ID NO:7):

They are specifically recognized by hybridization with the matrix-bound probes; normal oligo, A-mutated oligo and C-mutated oligo respectively.

The hybridization reaction is performed at 25° C. for 1 hour, in 20 mM phosphate buffer, pH 7.4, 300 mM NaCl, 0.5% SDS containing 0.1 pmol of nucleic acid to be detected, 5'-labeled with $^{32}$p. The matrix is then washed in the same buffer at 35° C. The detection is performed by autoradiography of the matrix on a photographic film. Under these conditions, hybridization of the target nucleic acid takes place only on the electrode bearing the oligonucleotide of strictly complementary sequence; no cross-hybridization can be detected.

The specific detection of a bridging mutation is thus possible by virtue of this matrix.

EXAMPLE 6
USE OF ULTRA-MICROELECTRODES

Figure 12:
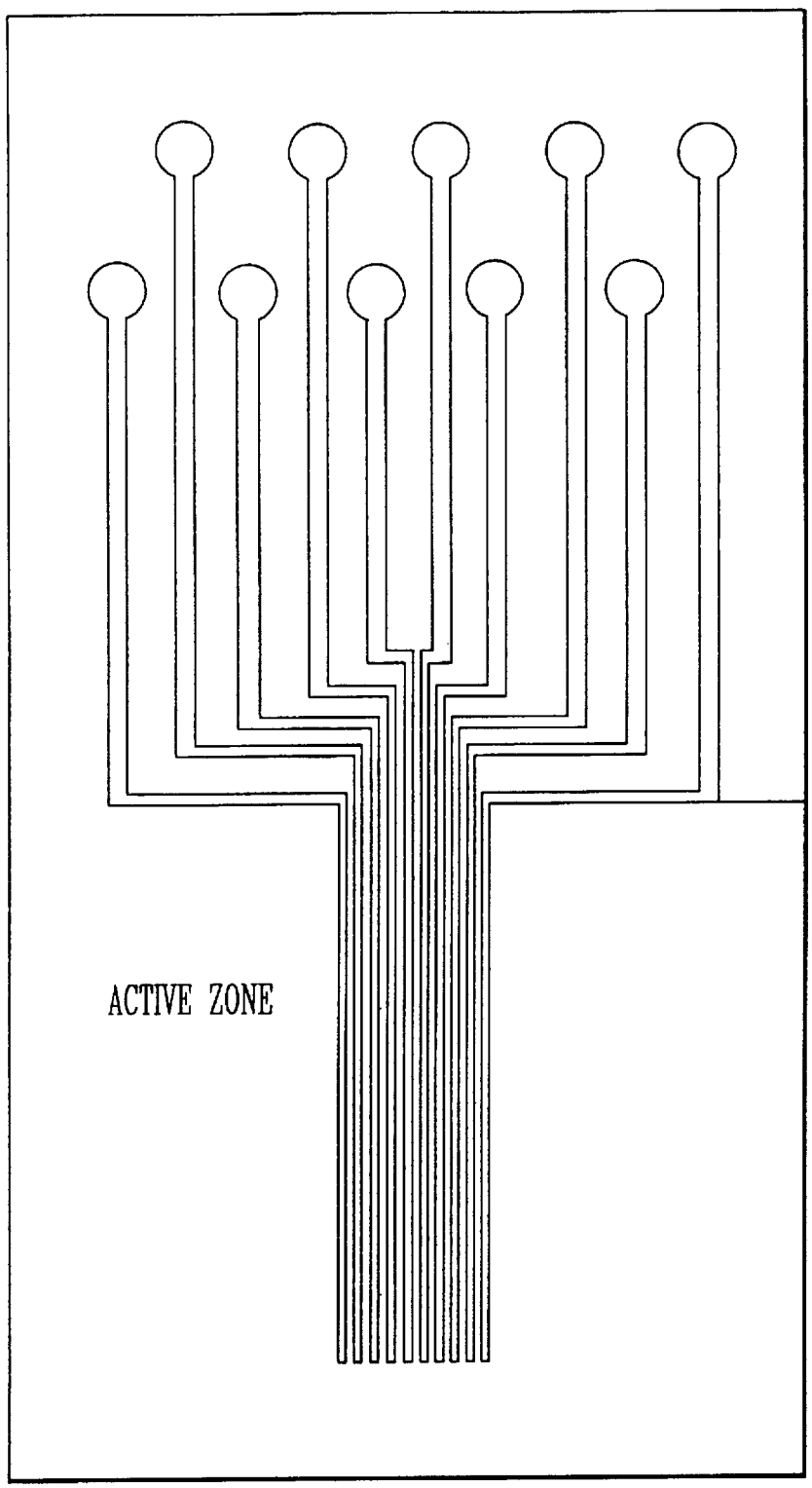
FIG. 12 illustrates an ultra-microelectrode according to Example 6.

A system represented in FIG. 12 is composed of 10 gold electrodes arranged on a glass plate; the width of the electrodes may vary from 10 to 100 µm and the length of the active zone (zone immersed in the solution) is of the order of 2 mm. Another system was manufactured by selective deposition of gold onto a silicon oxide insulating substrate, followed by insulation of the connections. Matrices consisting of square electrodes with a side length of 25 to 200 µm are thus obtained.

In both cases, the copolymerization of pyrrole and of oligonucleotide-pyrrole may be carried out on each electrode, according to the process described in Example 5, and the polypyrrole films obtained are of good quality and their thickness can be fully controlled, as described in Example 2.

EXAMPLE 7
IN SITU SYNTHESIS OF OLIGONUCLEOTIDES: ELECTROCHEMICAL DEPROTECTION OF 5'-TTCTGAGG-3'(SEQ ID NO:8)

The synthesis was carried out on an amino polypyrrole support (Compound No. 8), bearing an arm which is cleavable for the needs of subsequent analysis of the oligonucleotide formed.

PROCEDURE:
Synthesis of 5'-TTCTGAGG-3'(SEQ ID NO:8) with a step of electrochemical deprotection of 5'-TTCTGAGG-3'(SEQ ID NO:8)

Thymidine amidite, introduced in position (5) from the 3' end of the oligonucleotide, is deprotected by application of a potential of +1.1 V for 15 min when the protecting group is thiopixyl, or of −1.3 V for 15 min when the protecting group is the p-nitrobenzoyl group. The other nucleosides are introduced in the form of tritylated amidites, and are deprotected chemically, by detritylation with trichloroacetic acid.

Figure 13:
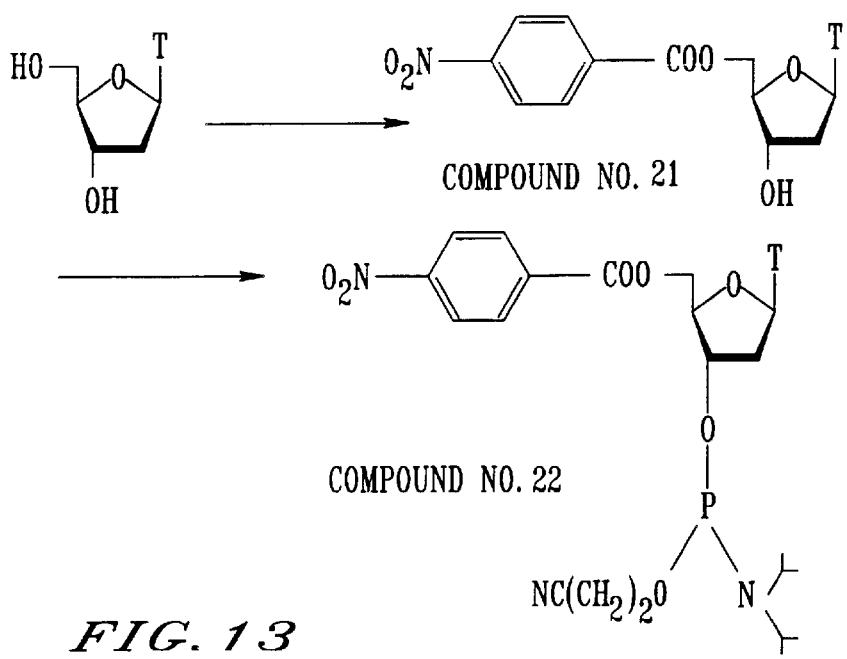
FIG. 13 illustrates the preparation of Compounds No. 21 and 22.

1) Protection with a p-Nitrobenzoyl Group:

The steps for the preparation of the protected nucleoside are illustrated by FIG. 13.

Synthesis of p-nitrobenzoylthymidine (Compound No. 21 : FIG. 13)

Thymidine (2.42 g; 10 mmol) is dried by coevaporation in pyridine, then taken up in 200 ml of anhydrous pyridine and cooled to 4° C. p-Nitrobenzoyl chloride (2.04 g; 11 mmol) is added. The temperature is allowed to rise and the reaction is left overnight at room temperature. The reaction is stopped with 5 ml of saturated sodium bicarbonate. The reaction mixture is concentrated and then taken up in 500 ml of chloroform. The organic solution obtained is washed with 2×500 ml of 0.5M $NaHCO_3$ and then with 250 ml of saturated NaCl. The aqueous phases are counter-extracted with 100 ml of $CHCl_3$. The organic phases are evaporated. The pure product is obtained by column chromatography on silica. It is eluted with 5% of methanol in chloroform. Yield=58%.

Synthesis of p-nitrobenzoylthymidine amidite (Compound No 22 : FIG. 13)

Compound No. 21 (1.96 g; 5 mmol) and diisopropylammonium tetrazolate (428 mg; 2.5 mmol) are dried by coevaporation using an anhydrous dichloromethane/acetonitrile solvent. These reagents are taken up in 25 ml of anhydrous dichloromethane and bis (diisopropylaminocyanoethoxy)phosphine (1.8 g; 6 mmol) is added. After reacting for 2 h (in the absence of oxygen and moisture) the reaction mixture is diluted with 250 ml of dichloromethane and washed successively with 2×250 ml of 0.5M sodium bicarbonate and with 250 ml of saturated sodium chloride. The organic phase is evaporated. The residue is taken up in 10 ml of dichloromethane. The product (Compound No. 22) is obtained by precipitation in hexane, then dried under vacuum and stored under argon. Yield=84%.

2) Protection with a Thiopixyl Group

The steps for the preparation of the protected nucleoside are illustrated by FIG. 14.

Synthesis of thiopixylthymidine (Compound No. 23: FIG. 14)

Thymidine (2.42 g; 10 mmol) is dried by coevaporation in pyridine, taken up in 100 ml of anhydrous pyridine, cooled to 4° C. and reacted with thiopixyl chloride (3.4 g; 11 mmol). After gradual rise of the temperature to room temperature, the reaction is left to continue overnight (8 to 12 h approximately). The reaction is stopped with 10 ml of $NaHCO_3$. The solvent is evaporated off and the residue is taken up in 250 ml of dichloromethane. The organic solution obtained is extracted with 2×250 ml of saturated $NaHCO_3$ and then with 250 ml of distilled water. The aqueous phases are counter-extracted with 100 ml of chloroform. The organic phase is evaporated. The product is purified on a column of silica with 0.5% TEA (triethylamine) in the solvents. It is finally eluted with 5% of methanol in dichloromethane (+0.5% TEA). Yield=52%.

Synthesis of thiopixylthymidine amidite (Compound No. 24, FIG. 14)

Compound No. 24 is prepared from Compound No. 23 (5 mmol) according to the same procedure as for Compound No. 22. Yield=78%.

3) Binding of the First Nucleoside

The steps for this binding are illustrated in FIG. 15.

This oligonucleotide is synthesized on a strip of platinum (3×10 mm) on which a mixture of pyrrole and aminoethylpyrrole (9:1) has been copolymerized.

The first nucleoside (position 1- 3' end) is coupled with aminoethylpyrrole (Compound No. 8) according to the methods described for the functionalization of the silica supports [K. MIYOSHI et al., Nucleic Acids Res.; 8, (22), 5473–5489 (1989)] starting with an activated ester, N-isobutyryl 2'deoxyguanosine (Compound No. 25: FIG. 13a).

Compound No. 26 (10 mg) is dissolved in 500 µl of acetonitrile. The functionalized-polypyrrole-coated platinum electrode and 1 µl of triethylamine are added. The reaction is agitated mechanically for 20 hours at room temperature. The grafted electrode (Compound No. 26) is removed and washed thoroughly with acetonitrile and then with dichloromethane.

The unreacted amine functions are blocked with acetic anhydride (10% in 500 µl of pyridine) for 6 hours. The grafted electrode is washed with pyridine and with methanol, and then dried.

4) Synthesis of the Oligonucleotide dTTCTGAGG

The grafted electrode is placed in an emptied OPC® column (APPLIED BIOSYSTEMS). Filling is completed with teflon chips so as to minimize the residual volume. The nucleosides in positions 2, 3 and 4 are added according to the instructions of the manufacturer (APPLIED BIOSYSTEMS) for the "1 µmol cycle" on a 381A synthesizer. Chemical deprotection of the dimethoxytrityl group between each step is performed with TCA in dichloromethane under the conditions recommended by the manufacturer.

The amidite in position 5 (Compound No. 22 or Compound No. 24) is coupled according to the same method as for the normal amidites, with a coupling time of 1 min. Oxidation of the phosphite triester bond created and capping are performed according to the standard procedure. The electrode is removed from the column and electrochemical deprotection is performed.

If Compound No. 22 is used, the p-nitrobenzoyl group is cleaved by immersing the electrode in the following electrolyte: 0.1M tetrabutylammonium perchlorate in methanol, and by applying a potential of −1.3 V for 15 min.

If Compound No. 24 is used, the thiopixyl is cleaved by applying a potential of +1.1 V for 15 min, the electrolyte being 0.1M tetrabutylammonium perchlorate in acetonitrile.

In both cases, after cleavage of the protecting group of the T nucleoside in position 5', the electrode is replaced in the column with the teflon chips, and the synthesis is continued by successively adding the amidites C (position 6), T (position 7) and T (position 8).

When the synthesis is complete, the oligonucleotide is cleaved from the support: the electrode is treated with 4×500 µl of 28% aqueous ammonia in a stoppered flask for 4×½ h. The 4 fractions are combined in a stoppered 4 ml Wheaton flask, and are left for 16 h at 55° C. in order to deprotect the oligonucleotide.

After coevaporation in the presence of TEA, an aliquot (¹⁄₁₀₀th) of the oligonucleotide obtained is 5'-labeled with $^{32}p$ in the presence of polynucleotide kinase and then analyzed by polyacrylamide gel electrophoresis. The acrylamide gel electrophoresis analysis shows the presence of the desired product (octamer) and the absence of the oligonucleotide (pentamer), the presence of which would indicate poor electrochemical deprotection of the thymidine amidite.

We claim:

1. A process for preparing an electrically conductive copolymer represented by general formula (1):

comprising copolymerizing a monomer represented by formula (IV):

with a polymerizable monomer represented by the formula A, wherein said monomer A produces an electrically conductive polymer when polymerized, and represents a polymerized unit of said monomer A in the electrically conductive copolymer, represents either (1) a nucleotide unit or an analog thereof, or (2) an oligonucleotide unit or an analog thereof, x, y and z each, independently, represents an integer equal to or greater than 1, and l represents a covalent bond or a spacer arm.

2. The process of claim 1, wherein the copolymerization is an electrochemical copolymerization.

3. The process of claim 2, further comprising coupling additional units to the units of the copolymer.

4. The process of claim 3, wherein the coupling of additional units to the units of the copolymer comprises at least one electrochemical reaction.

5. The process of claim 4, wherein the copolymerization is conducted on the surface of an electrode.

6. The process of claim 1 wherein A is a pyrrole.

7. The method of claim 1, wherein A is acetylene, azine, p-phenylene, p-phenylene vinylene, pyrene, thiophene, furan, selenophene, pyridazine, carbazole or aniline.

8. The method of claim 1, wherein the ratio x/y is between 1/5 and 1/100,000.

9. The method of claim 1, wherein l is a spacer arm represented by the formula:

$$-R_1-[(CH_2)_n-R_2]_x-[(CH_2)_m-R_3]_y-(CH_2)_p-$$

wherein n is an integer from 1 to 10;
m is 0 or an integer from 1 to 10;
p is 0 or an integer from 1 to 10;
x is 0 or an integer from 1 to 8;
y is 0 or an integer from 1 to 8;

$R_1$, $R_2$ and $R_3$, which may be identical or different, represent: $CH_2$, O, S, NR', CO, CH=CH, NR'CO, CONR', $NHSO_2$, or $$-O-\overset{\overset{O}{\|}}{\underset{OR'}{P}}-O-$$

where R' represents a hydrogen atom or a $C_1$ to $C_{12}$ alkyl group.

* * * * *

UNITED STATES PATENT AND TRADEMARK OFFICE
CERTIFICATE OF CORRECTION

PATENT NO.    : 5,837,859
DATED         : November 17, 1998
INVENTOR(S)   : Robert Teoule et al.

It is certified that error appears in the above-identified patent and that said Letters Patent is hereby corrected as shown below:

Column 19,
Line 67, "represents a polymer-" beginning with a new paragraph, should read -- [A] represents a polymer- --.

Column 20,
Line 51, "represents either (1)" should read -- [B] represents either (1) --.

Signed and Sealed this

Second Day of October, 2001

Attest:

NICHOLAS P. GODICI
*Attesting Officer*    *Acting Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:1:

TGTACCTGAA TCGTCCGCCA T                                                    21

( 2 ) INFORMATION FOR SEQ ID NO:2:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:2:

TCCTCCTGGC CGG                                                             13

( 2 ) INFORMATION FOR SEQ ID NO:3:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:3:

TCCTCCAGGC CGG                                                             13

( 2 ) INFORMATION FOR SEQ ID NO:4:

( i ) SEQUENCE CHARACTERISTICS:
      ( A ) LENGTH: 13 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:4:

TCCTCCCGGC CGG                                                             13

( 2 ) INFORMATION FOR SEQ ID NO:5:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear

```
        ( i i ) MOLECULE TYPE: other nucleic acid
                ( A ) DESCRIPTION: /desc = "SYNTHETIC OLIGONUCLEOTIDE"

( x i ) SEQUENCE DESCRIPTION: SEQ ID NO:5:

CTGTTGGACA  TCCTGGATGC  CGGCCAGGAG  GAGTACAGCG  CCATGCGCGA  C                              51

( 2 ) INFORMATION FOR SEQ ID NO:6:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC OLIGONUCLEOTIDE"

( x i ) SEQUENCE DESCRIPTION: SEQ ID NO:6:

CTGTTGGACA  TCCTGGATGC  CGGCCTGGAG  GAGTACAGCG  CCATGCGCGA  C                              51

( 2 ) INFORMATION FOR SEQ ID NO:7:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC OLIGONUCLEOTIDE"

( x i ) SEQUENCE DESCRIPTION: SEQ ID NO:7:

CTGTTGGACA  TCCTGGATGC  CGGCCGGGAG  GAGTACAGCG  CCATGCGCGA  C                              51

( 2 ) INFORMATION FOR SEQ ID NO:8:

( i ) SEQUENCE CHARACTERISTICS:
                ( A ) LENGTH: 8 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "SYNTHETIC OLIGONUCLEOTIDE"

( x i ) SEQUENCE DESCRIPTION: SEQ ID NO:8:

TTCTGAGG                                                                                    8
```